(12) United States Patent
Wigh et al.

(10) Patent No.: US 8,485,035 B2
(45) Date of Patent: Jul. 16, 2013

(54) METHOD OF DETECTING DEFECTS

(75) Inventors: Jeffrey B. Wigh, St. Joseph, MO (US); Richard L. Ebersold, St. Joseph, MO (US); Troy L. Elbert, St. Joseph, MO (US); Timothy J. Coolman, Savannah, MO (US)

(73) Assignee: Herzog Services, Inc., St. Joseph, MO (US)

( * ) Notice: Subject to any disclaimer, the term of this patent is extended or adjusted under 35 U.S.C. 154(b) by 0 days.

(21) Appl. No.: 13/590,962

(22) Filed: Aug. 21, 2012

(65) Prior Publication Data

US 2013/0152691 A1 Jun. 20, 2013

Related U.S. Application Data

(60) Provisional application No. 61/526,094, filed on Aug. 22, 2011.

(51) Int. Cl.
*G01N 29/04* (2006.01)

(52) U.S. Cl.
USPC ............................................. 73/636; 73/649

(58) Field of Classification Search
USPC .................... 73/636, 596, 628, 632, 634, 649
See application file for complete search history.

(56) References Cited

U.S. PATENT DOCUMENTS

| | | | |
|---|---|---|---|
| 3,771,354 A | 11/1973 | Miller | |
| 4,040,738 A | 8/1977 | Wagner | |
| 4,165,648 A | 8/1979 | Pagano | |
| 4,174,636 A | 11/1979 | Pagano | |
| 4,217,782 A | 8/1980 | Pont | |
| 4,235,112 A | 11/1980 | Kaiser | |
| 4,429,576 A | 2/1984 | Norris | |
| 4,457,178 A | 7/1984 | Turbe et al. | |
| 4,468,966 A | 9/1984 | Bradshaw | |
| 4,487,071 A | 12/1984 | Pagano et al. | |
| 4,532,796 A | 8/1985 | Martens et al. | |
| 4,559,825 A | 12/1985 | Martens | |
| 4,593,569 A | 6/1986 | Joy | |
| 4,662,224 A | 5/1987 | Turbe | |
| 4,700,574 A | 10/1987 | Turbe | |
| 5,020,371 A | 6/1991 | Panetti | |
| 5,419,196 A | 5/1995 | Havira et al. | |
| 5,497,662 A | 3/1996 | Dykes | |
| 5,521,707 A * | 5/1996 | Castore et al. | ................ 356/394 |
| 5,712,706 A * | 1/1998 | Castore et al. | ................ 356/394 |
| 6,055,862 A | 5/2000 | Martens | |
| 7,036,232 B2 | 5/2006 | Casagrande | |
| 7,054,762 B2 | 5/2006 | Pagano et al. | |
| 7,849,748 B2 | 12/2010 | Havira | |

(Continued)

*Primary Examiner* — Jacques M Saint Surin
(74) *Attorney, Agent, or Firm* — Erickson Kernell Derusseau & Kleypas, LLC

(57) ABSTRACT

A method for detecting defects in a railway rail including a search unit and preferably a roller search unit ("RSU") mounted on a test vehicle and in rolling contact with the running surface of the rails to inspect each rail. The RSU includes a tire filled with a liquid and a transducer assembly mounted within the tire. The transducer assembly includes one or more arrays of ultrasonic transducers directed toward the running surface of the rail. A laser profiler mounted on the test vehicle in combination with a linear encoder provide profile data which is communicated to a system controller to dynamically adjust the focal laws for the one or more arrays of transducers to dynamically steer the transmitted beams to produce the ideal inspection beam sets while the test vehicle is in motion.

20 Claims, 10 Drawing Sheets

U.S. PATENT DOCUMENTS

| | | |
|---|---|---|
| 7,882,742 B1 | 2/2011 | Martens |
| 8,418,563 B2 * | 4/2013 | Wigh et al. ............... 73/649 |
| 8,424,387 B2 * | 4/2013 | Wigh et al. ............... 73/649 |
| 2012/0218868 A1 * | 8/2012 | Kahn et al. ............... 367/99 |

* cited by examiner

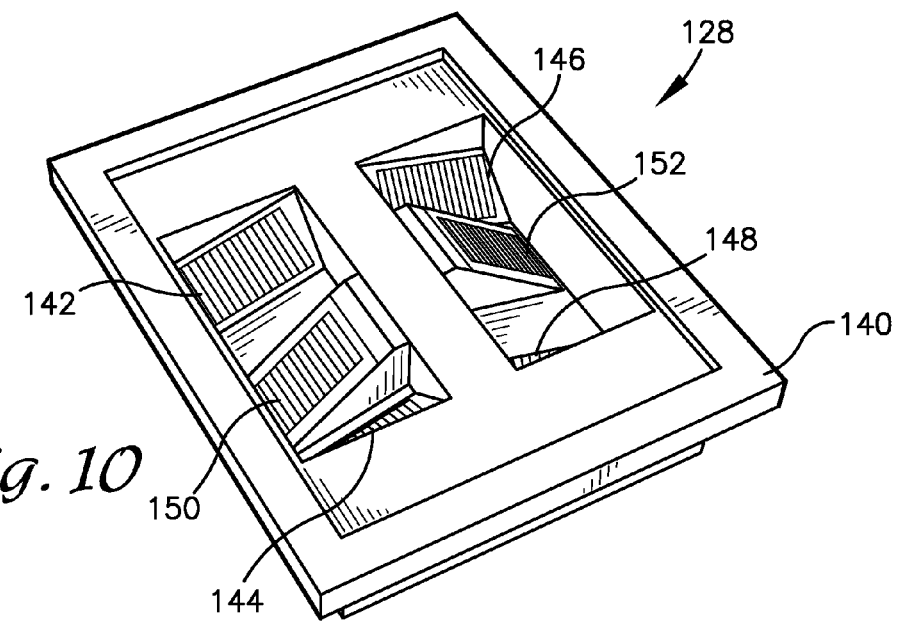
Fig. 10
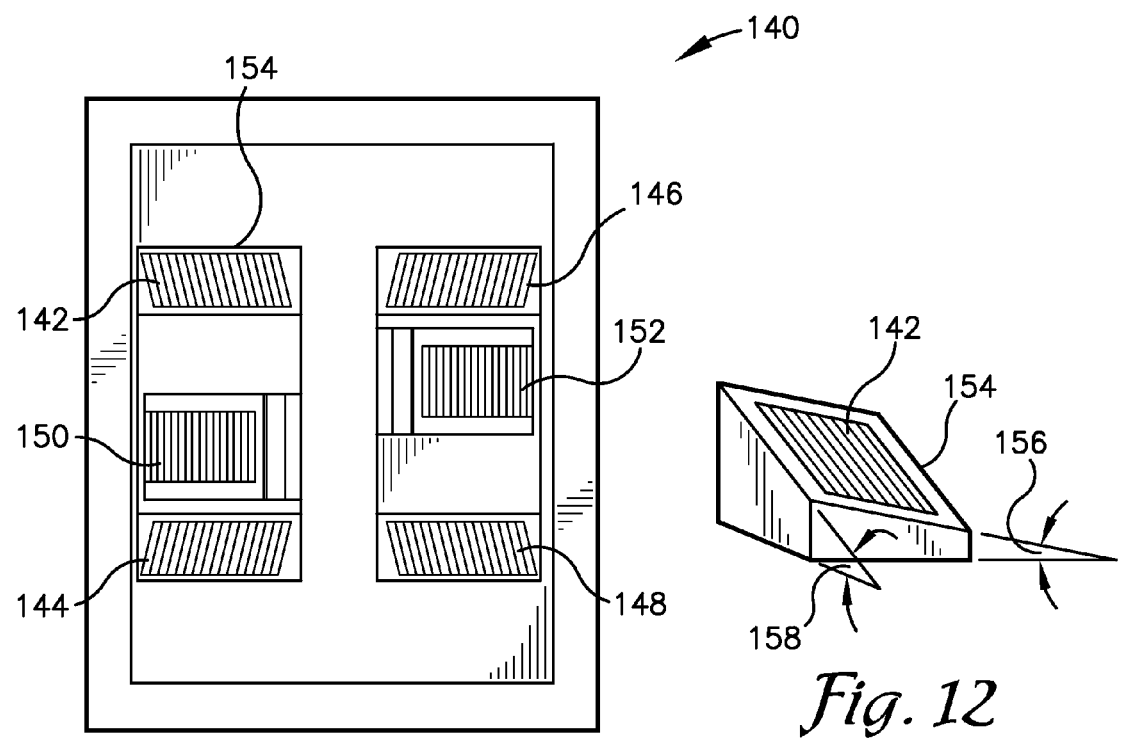
Fig. 11
Fig. 12

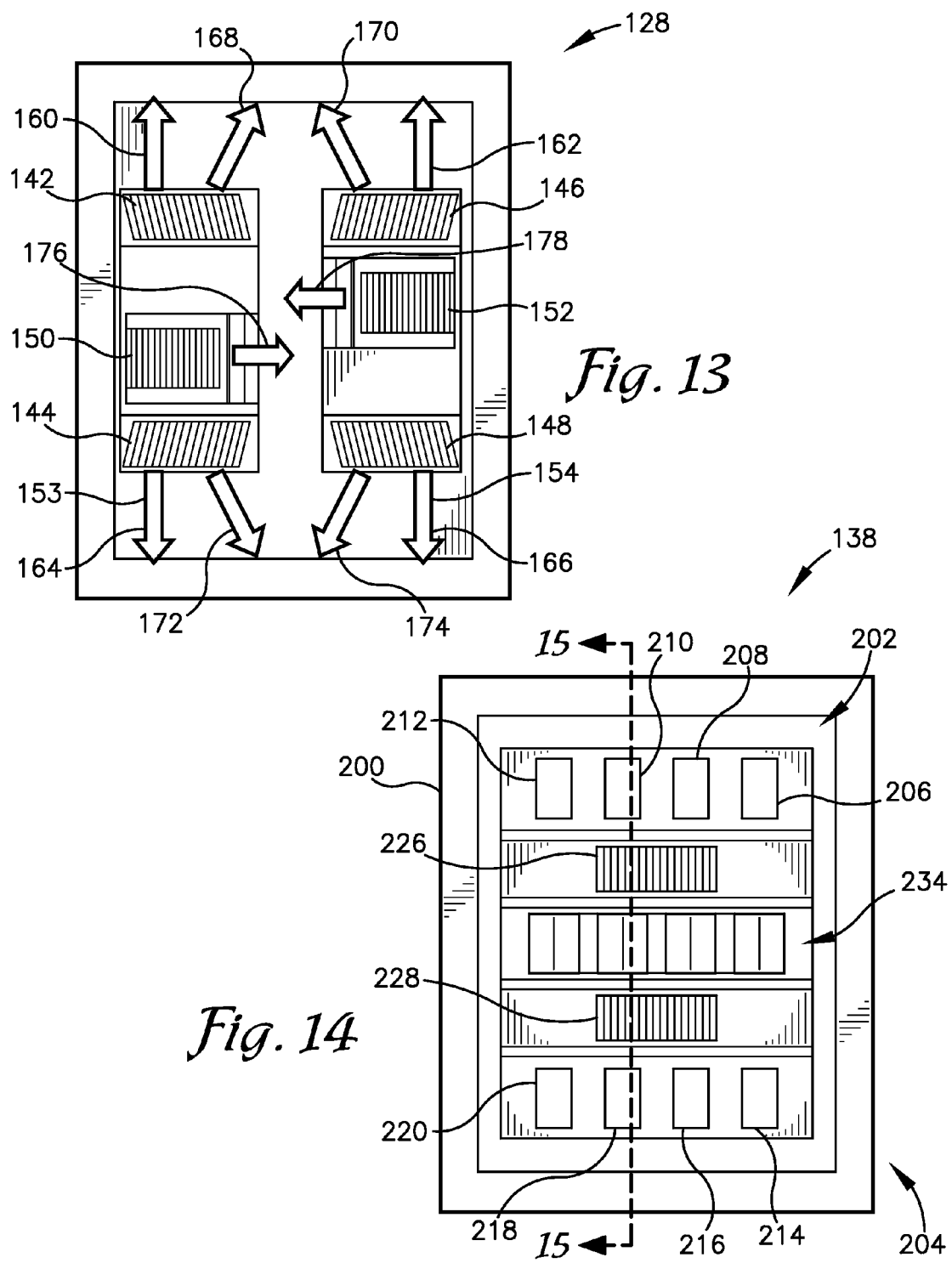

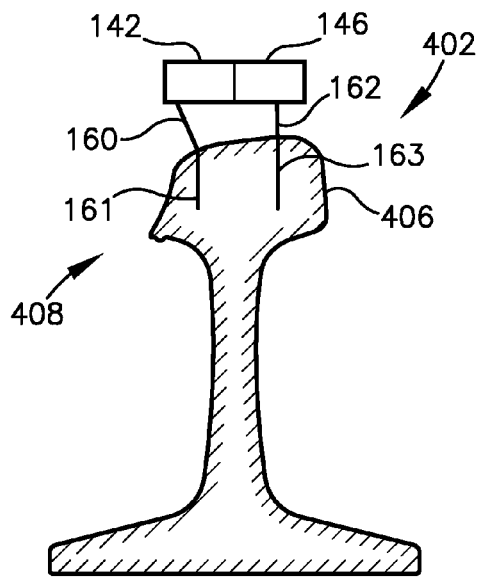
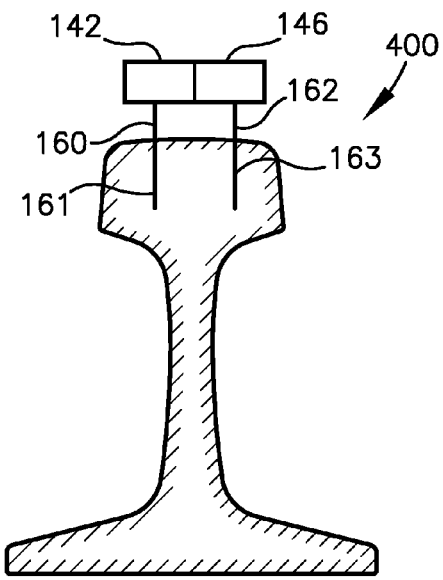
Fig. 17
Fig. 18
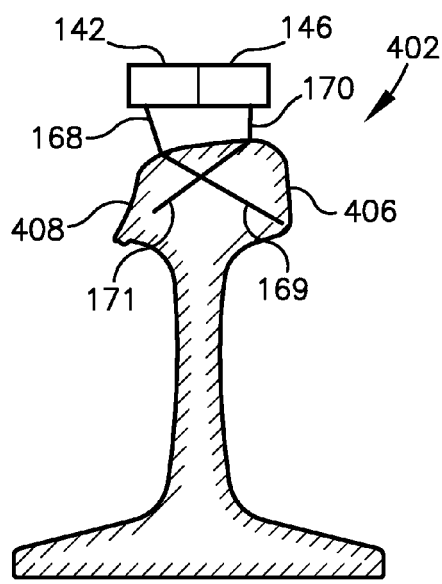
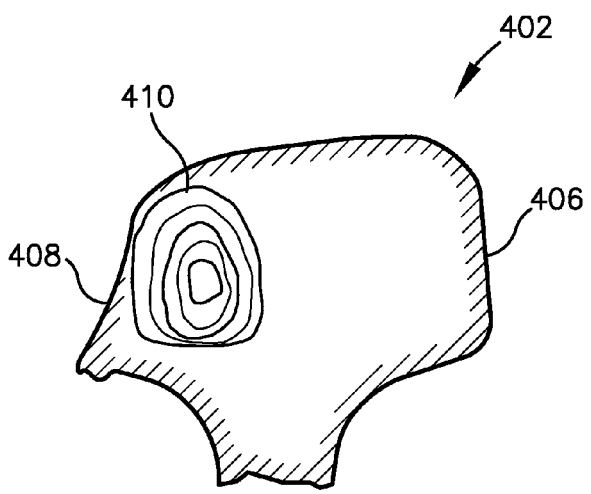
Fig. 19
Fig. 20

METHOD OF DETECTING DEFECTS

CROSS-REFERENCE TO RELATED APPLICATIONS

This application claims the benefit of co-pending application Ser. No. 61/526,094, filed on Aug. 22, 2011, entitled ULTRASONIC INSPECTION SYSTEM.

FIELD

The present invention generally relates to a method of detecting defects in a structure and, more particularly, to a method of performing nondestructive-type testing in situ using ultrasonic transducers to detect flaws and defects in a railway rail.

BACKGROUND

The United States Federal Railroad Administration has published statistics which indicate that train accidents caused by track failures including rail, joint bar and anchoring resulted in approximately 1,300 derailments from 2001 to 2011. The primary cause of these track failures was defects and fissures in the rail head.

During their normal use and as would be expected, the rail portions of most track structures will be subjected to severe, and uncontrollable environmental conditions. These severe environmental conditions, over a relatively long period of time, may ultimately result in such rail developing certain detrimental flaws.

In addition, in today's modern railroad industry, the rail portion of such track structures will quite often be required to support rather heavy loads being carried by modern freight cars. Furthermore, these heavy loads are travelling at relatively high speeds. It would not be uncommon for these freight cars, when they are fully loaded with cargo, to weigh up to generally about 125 tons. Such relatively heavy loads and high speeds can, also, result in undesirable damage to such rail portions of the track structure. Such damage, for example, may include stress fractures.

It would be expected, therefore, that if these detrimental defects were not timely detected and, likewise, if they are left unrepaired such defects could lead to some rather catastrophic disasters, such as, a train derailment.

As is equally well known, such train derailments are not only costly to the railroad industry from the standpoint of the damage that will likely be incurred to both the cargo being transported and to the railway equipment itself, but, even more importantly, such train derailments may also involve some rather serious injuries, or even worse death, to railway personnel and/or other persons who may be in the vicinity of a train derailment.

It is further well known that a relatively large number of these train derailments have resulted in the undesirable and often costly evacuation of nearby homes and businesses. Such evacuation may be required, for example, when the cargo being transported involves certain highly hazardous chemical products. These hazardous chemical products will generally include both certain types of liquids, such as corrosive acids, and certain types of toxic gases, such as chlorine.

To detect such flaws and defects, ultrasonic testing has been employed. Vehicles have been built which travel along the track and continuously perform ultrasonic testing of the track. These vehicles carry test units which apply ultrasonic signals to the rails, receive ultrasonic signals back from the rails, and provide indications of flaws and defects.

Some of these systems employ small, thin-walled tires which roll along the rails. They are pressed down against the rail so as to have a flat area in contact with the rail. These tires contain acoustic transducers and are filled with a liquid, usually a water-glycol solution. The transducers are arranged at various angles to produce acoustic beams which travel through the mounting substrate and liquid and are directed toward the rail surface. The angles are predetermined based on the known geometry of a new rail. The high frequency electrical transducers are pulsed with energy and the generated beams pass through the material of the liquid and tire into the rail. The angle of incident of the beam with respect to the rail surface is predetermined based on the desired angle of refraction in a known material, assuming a horizontal head shape according to Snell's law.

Only a few transducers can be mounted to the substrate due to spatial considerations. Also, the angles of the acoustic beams produced by the transducers are dictated by their fixed mounting angle. The rail head may be worn or deformed by the massive loads and stresses to which it is subjected. The shape of the rail head may change over time whereby the running surface of the rail head is no longer substantially horizontal. Because many of the inspection systems employ ultrasonic transducers mounted in a fixed position at a fixed angle relative to a presumed horizontal inspection surface, the resulting beam inspection angles may not be optimal and may fail to detect defects in the rail.

SUMMARY

The present invention provides an apparatus for detecting defects in a railway rail. The apparatus includes a search unit and preferably a roller search unit ("RSU") mounted on a test vehicle and in rolling contact with the running surface of the rails to inspect each rail. The RSU includes a tire filled with a liquid and a transducer assembly mounted within the tire. The transducer assembly includes one or more arrays of ultrasonic transducers directed toward the running surface of the rail. The liquid provides a coupling between the transducers through the tire wall and into the rail. Beams transmitted by the one or more arrays of ultrasonic transducers may be dynamically adjusted to compensate for the varying profile of the rail head and running surface. A laser profiler mounted on the test vehicle in combination with a linear encoder provide profile data which is communicated to a system controller to dynamically adjust the focal laws for the one or more arrays of transducers to steer the transmitted beams to produce the ideal inspection beam sets while the test vehicle is in motion.

The ultrasonic phased array transducers including one or more transducer assemblies with 8 to 256 individual elements that are individually controlled may be used to effectively steer the inspection beam. The elements may be arranged in a strip (linear array), a square matrix (2-D array), a ring (annular array), a circular matrix (circular array), or other more complex shapes.

An ultrasonic phased array transducer system varies the time between the pulsing of individual elements of the array in such a way that the individual waves from each individual element combine in predictable ways to steer or shape the beam emitted from the array. This is accomplished by pulsing the individual elements at calculated times. Based on the focal law of the array, the properties of the transducer assembly, the transmission medium and the geometry and acoustical properties of the test material, the beam can be dynamically steered through various angles and focal distances. Beam steering is accomplished in a fraction of a second allowing the beam to be steered to the optimal angle based on the orientation of the test material, such as a rail head, to scan from multiple angles, sweep over a range of angles, or scan at multiple focal depths. The ultrasonic phased array transducer can spatially sort a returning wave front according to the arrival time and amplitude at each element to be processed and displayed.

The output from profiling sensors such as one or more laser transceivers or cameras are combined to determine the geometric profile of the rail, which is used by the system to determine the focal laws for the desired target of the ultrasonic beams generated by the ultrasonic phased array transducers.

BRIEF DESCRIPTION OF THE DRAWINGS

FIG. 10 is a perspective view of a phase array ultrasonic transducer assembly.

FIG. 11 is a plan view of the phased array ultrasonic transducer assembly of FIG. 10.

FIG. 12 is a perspective view of a phased array ultrasonic transducer from the assembly of FIG. 10.

FIG. 13 is an illustration of beams generated from the ultrasonic phased array assembly of FIG. 11.

FIG. 14 is a plan view of an ultrasonic transducer assembly.

FIG. 17 is an illustration of beams generated by phased array ultrasonic transducers for a worn rail head.

FIG. 18 is an illustration of beams generated by phased array ultrasonic transducers for a rail head.

FIG. 19 is an illustration of beams generated by phased array ultrasonic transducers for a worn rail head.

FIG. 20 is an enlarged partial sectional view of a worn rail head illustrating a defect.

DESCRIPTION

As required, detailed embodiments of the present invention are disclosed herein. However, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for the claims and/or as a representative basis for teaching one skilled in the art to variously employ the present invention.

Moreover, except where otherwise expressly indicated, all numerical quantities in this description and in the claims are to be understood as modified by the word "about" in describing the broader scope of this invention. Practice within the numerical limits stated is generally preferred. Also, unless expressly stated to the contrary, the description of a group or class of materials as suitable or preferred for a given purpose in connection with the invention implies that mixtures or combinations of any two or more members of the group or class may be equally suitable or preferred.

Figure 1:
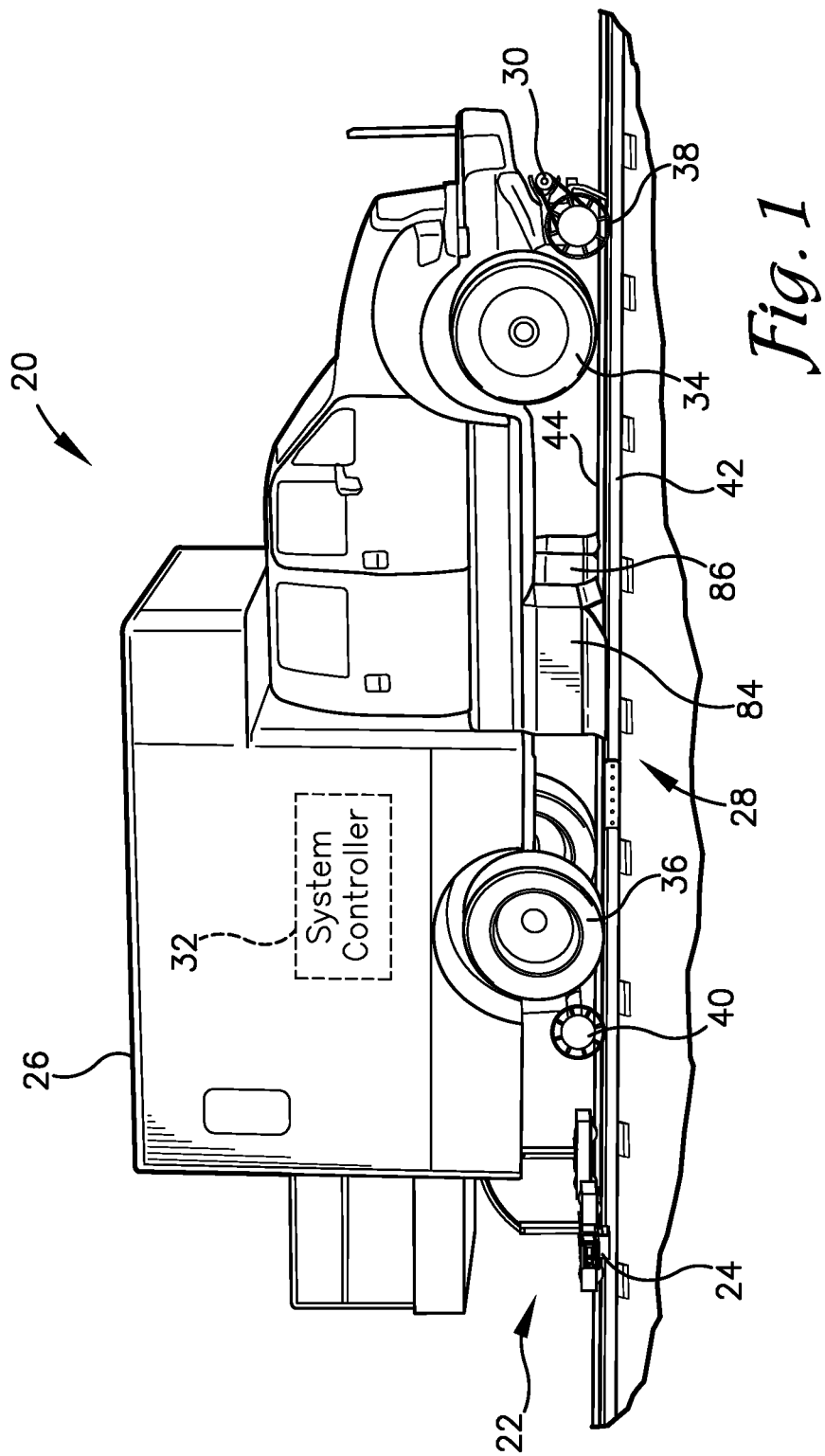
FIG. 1 is an illustration of a test vehicle with an ultrasonic inspection system of the present invention.
Figure 2:
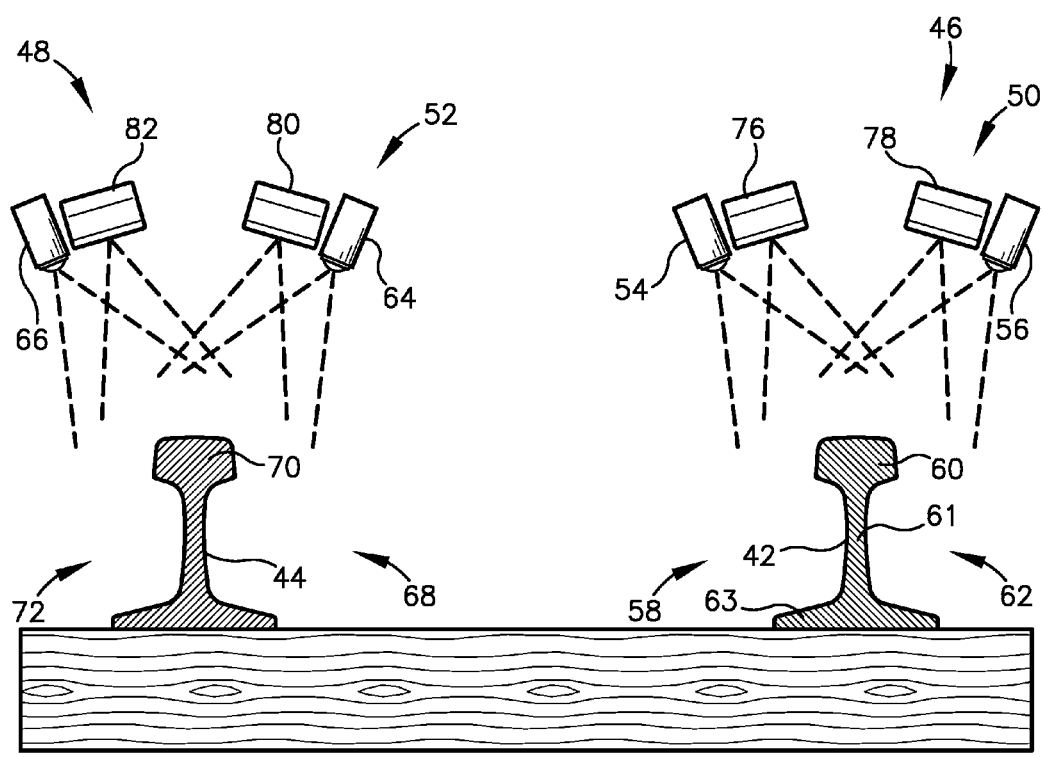
FIG. 2 is a diagrammatic illustration of a rail profiler system.
Figure 3:
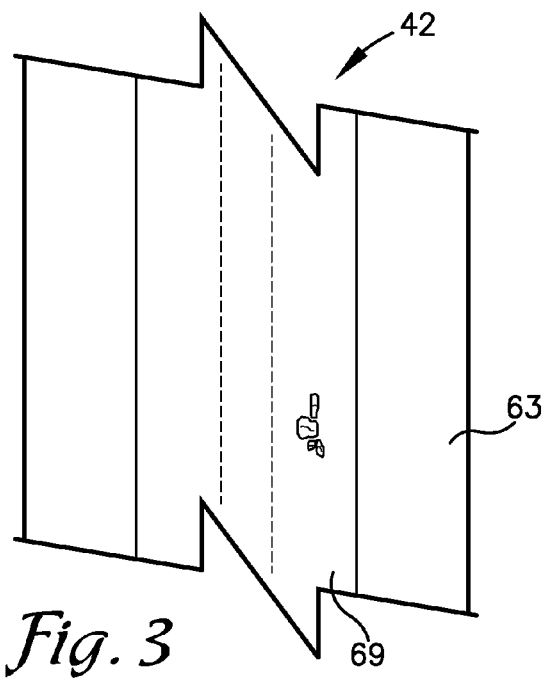
FIG. 3 is a partial plan view of a rail head.

Referring initially to FIGS. 1 and 2, a rail inspection apparatus unit is generally indicated by reference numeral 20. The rail inspection apparatus includes a carriage 22 for supporting test assemblies 24 mounted behind a test vehicle 26, a profiler system 28 mounted under the test vehicle 26, and an encoder 30, all of which are coupled to a system controller 32 mounted inside the test vehicle 26.

The test vehicle 26 includes front 34 and rear 36 rubber tires and flanged rail wheels 38 and 40. The flanged rail wheels 38 and 40 engage rails 42, 44 when the test vehicle 26 is in a hi-rail configuration. In the hi-rail configuration the front tires 34 are not in contact with the ground or rails 42 and 44, and the front of the test vehicle 26 is supported on the front flanged rail wheels 38. The rear tires 36 are in contact with the rails 42 and 44 to drive the test vehicle 26 along the rails 42 and 44. The encoder 30 is coupled to the front flanged rail wheels 38.

The encoder 30 outputs information to the test assemblies 24 and profiler system 28, which is used to determine position. The encoder 30 is preferably a linear encoder that outputs a digital signal corresponding to the rotation of the flanged rail wheel 38. The encoder 30 outputs a signal which corresponds to the rotation of the rail wheel 38, which in turn is used to calculate the position of the test vehicle 26.

Referring to FIGS. 1 and 2, the profiler system 28 includes two pairs of laser transceivers 46 and 48, and may also include two pairs of line scan cameras 50 and 52, each of which is directed at rails 42 and 44, respectively. The laser pair 46 includes a gauge side laser transceiver 54 and a field side laser transceiver 56 directed at rail 42. Gauge side laser transceiver 54 scans the gauge side 58 of the rail 42, including the web and base, across the rail head 60. The field side laser transceiver 56 scans the field side 62 of the rail 42, including the web and base, across the rail head 60. Likewise, laser transceiver pair 48 includes a gauge side laser transceiver 64 and a field side laser transceiver 66 directed at rail 44. Gauge side laser transceiver 64 scans the gauge side 68 of the rail 44, including the web and base, across the rail head 70. The field side laser transceiver 66 scans the field side 72 of the rail 44, including the web and base, across the rail head 70. Each laser transceiver may scan at a fixed rate or frequency or may be triggered by the encoder 30 output. A laser profiling system such as a LMI Gocator 2050 available from LMI Technologies may be used.

Line scan camera system 50 includes a gauge side line scan camera 76 and a field side line scan camera 78 directed at rail 42. The gauge side line scan camera 76 captures a line or column of data of the gauge side 58 of the rail 42. The field side line scan camera 78 captures a line or column of data of the field side 62 of the rail 42. Likewise, the line scan camera system 52 include a gauge side line scan camera 80 and a field side line scan camera 82 directed at rail 44. The gauge side line scan camera 80 captures a line or column of data of the gauge side 68 of the rail 44 while the field side line scan camera 82 captures a line or column of data of the field side 72 of the rail 44. Line scan cameras such as a Basler Runner series available from Basler Vision Technologies may be used.

Each of the line scan cameras 76, 78, 80 and 82 may be triggered by the encoder 30 output or scan at a set frequency such as 27,000 Hz, depending on the hardware selected and the storage capacity of the system. It should be understood that other frequencies and resolutions may be used for the line scan cameras and laser transceivers. Additionally, other image systems may be used such as a high definition video system, for example.

The pair of laser transceivers 46 and line scan cameras 50 may be surrounded by a housing 84. Laser transceivers 48 and line scan cameras 52 may be surrounded by a housing 86. Each housing 84 and 86 encloses the laser transceivers and line scan cameras on the four vertical sides and top to protect the lasers and cameras from the environment, to improve the performance of the lasers and cameras in all ambient lighting conditions and to protect the eyes of any individuals working or located around the test vehicle 26.

Referring to FIGS. 6-9, the carriage assembly 22 includes right 100 and left 102 carriages. The right 100 and left carriages 102 are connected together by a cross member 104, which includes a pneumatic or hydraulic cylinder 106 to adjust the width of the carriage 22 as necessary to engage the rails 42 and 44. The left carriage 102 is a mirror image of the right carriage 100 so only the right carriage will be described in detail, it being understood that the same detailed description applies to the left carriage 102.

The right carriage 100 includes a pair of flanged rail wheels 107, which support the carriage 100 on the rail 42. The flanged rail wheels 107 are mounted to a frame 109, to which a first roller search unit ("RSU") assembly 108 and a second RSU assembly 110 is mounted. Nylon, Teflon® or other high density polymer blocks 112 are mounted between the flanged rail wheels 107 and the RSUs 108 and 110. Spray nozzles 114 are mounted in the polymer blocks 112 and directed toward the running surface of the rail head 60 and the adjacent RSU 108 or 110. The polymer blocks 112 provide protection for the RSUs 108 and 110. The spray nozzles 114 spray a liquid such as water or a water/ethylene glycol mixture on the running surface of the rail head 60 to remove debris and to improve the contact of the RSUs 108 and 110 with the running surface 69 of the rail 42.

RSU assembly 108 includes a tire 120 mounted on a wheel 122, which rotates with the tire 120 about an axle 124. The tire is clamped to the wheel 122 at its bead 121 and includes a circumferential contact surface or tread 123, which makes contact with the running surface 69 of the rail head 60. The axle 124 is mounted to the frame 109. The tire 120 contains a coupling liquid 126 such as a water/ethylene glycol mixture. A transducer assembly 128 may be positioned within the tire 120 and coupled to the axle 124. The transducer assembly 128 includes a lower planar surface 129, which is mounted facing the circumferential contact surface 123 of the tire 120, and is maintained in a plane generally parallel to the running surface 69 of the rail head 60 at a fixed distance.

RSU assembly 110 includes a tire 130 mounted on a wheel 132, which rotates with the tire 130 about an axle 134. The axle 134 is mounted to the frame 109. The tire is clamped to the wheel 132 at its bead 131 and includes a circumferential contact surface or tread 133, which makes contact with the running surface 69 of the rail head 60. The tire 130 contains a coupling liquid 136 such as a water/ethylene glycol mixture. A transducer assembly 138 may be positioned within the tire 130 and coupled to the axle 134. The transducer assembly 138 includes a lower planar surface 139, which is mounted facing the circumferential contact surface 133 of the tire 130, and is maintained in a plane generally parallel to the running surface 69 of the rail head 60 at a fixed distance.

Referring to FIGS. 9-13, the transducer assembly 128 includes a transducer mount 140, which may be formed from a high strength plastic, epoxy, resin, Noryl® resin blend of polyphenylene oxide and polystyrene ("PPO"), polyphenylene ether ("PPE") resin, or a PPE/olefin resin blend, for example.

Conventional ultrasonic transducers typically consist of a single transducer that generates and receives ultrasonic sound waves, or a pair of transducers, one generating sound waves and the other receiving the echo returns. Phased array transducers typically include a transducer assembly with 8 to 256 individual elements that are individually controlled. The elements may be arranged in a strip (linear array), a square matrix (2-D array), a ring (annular array), a circular matrix (circular array), or other more complex shapes. The transducers typically operate at frequencies from 1 MHz to 10 MHz, for example.

The ultrasonic phased array transducer system varies the time between the pulsing of individual elements of the array in such a way that the individual waves from each individual element combine in predictable ways to steer or shape the beam from the array. This is accomplished by selectively energizing or pulsing the individual elements at independent times. These respective delays are referred to as delay laws and/or focal laws. Based on the focal law of the array, the properties of the transducer assembly mount, the transmission medium and the geometry and acoustical properties of the test material, the beam can be dynamically steered through various angles and focal distances. Beam steering is accomplished in a fraction of a second allowing the beam to be steered to the optimal angle based on the orientation of the test material, such as a rail head, to scan from multiple angles, sweep over a range of angles, or scan at multiple focal depths. The ultrasonic phased array transducer can spatially sort a returning wave front according to the arrival time and amplitude at each element to be processed and displayed.

The transducer assembly 128 includes four ultrasonic phased array transducers 142, 144, 146 and 148 secured to the mount 140 for generating ultrasonic acoustic beams forward and backward longitudinally generally parallel to a longitudinal axis X of the rail 42 and acoustic beams across the rail 42 at an angle relative to the longitudinal axis X from both the gauge side 58 and the field side 62 to detect under shell defects. The transducer assembly 128 also includes two ultrasonic phased array transducers 150 and 152, secured to the mount 140, directed laterally or transversely relative to a lateral axis Y across the rail head 60 from both the gauge side 58 and field side 62, to detect vertical split head ("VSH") defects.

The forward facing ultrasonic phased array transducers 142 and 146 are mounted on the transducer mount 140 on a compound symmetric wedge shape wherein surface 154 is formed or cut at two different angles, for example, a wedge angle 156 and a roof angle 158. Wedge angle 156 may be between zero and 30 degrees and roof angle 158 may be between 10 and 55 degrees, for example. The backward facing ultrasonic phased array transducers 144 and 148 are symmetrically secured to the transducer mount 140 at the same angles as the corresponding forward facing ultrasonic phased array transducers 142 and 146. The laterally facing ultrasonic phased array transducers 150 and 152 are secured to the transducer mount 140 at a roof angle of between about 10 and 55 degrees and a wedge angle of between about zero and 30 degrees, for example. For clarity, the ranges stated herein are stated as positive ranges, but it should be understood that a range includes a corresponding negative range or +/− a range.

In the exemplary embodiment, ultrasonic phased array transducers 142 and 146 are secured to transducer mount 140 such that beams 160 and 162, when viewed from above, are emitted parallel to rail 42 and when viewed in elevation view are emitted at an angle to produce a resultant beam in the rail 42 of about 60 to 80 degrees from vertical. Likewise, ultrasonic phased array transducers 144 and 148 emit beams 164 and 166 parallel to rail 42 in the opposite direction from beams 160 and 162 when viewed from above, and at an angle to produce a resultant beam in the rail 42 of about 60 to 80 degrees from a vertical axis Z when viewed in elevation.

Ultrasonic phased array transducers 142 and 146 also emit ultrasonic beams 168 and 170 directed generally parallel to rail 42 when viewed from above, each crossing the rail 42 in opposite directions at an angle to produce a resultant beam in the rail 42 of about 10 to 30 degrees. When viewed in elevation view, beams 168 and 170 descend into rail 42 at an angle to produce a resultant beam in the rail 42 of about 60 to 80 degrees from vertical. Likewise, ultrasonic phased array transducers 144 and 148 also emit beams 172 and 174 directed generally parallel to rail 42 when viewed from above, each crossing the rail 42 in opposite directions at an angle to produce a resultant beam in the rail 42 of about 10 to 30 degrees. When viewed in elevation view, beams 172 and 174 descend into rail 42 at an angle to produce a resultant beam in the rail 42 of about 60 to 80 degrees from vertical. Ultrasonic beams 168, 170, 172 and 174 provides a view of under shell defects in the rail head 60 from both the gauge side 58 and the field side 62.

Ultrasonic phased array transducers 150 and 152 emit ultrasonic beams 176 and 178 which are directed downward at an angle to produce a resultant beam in the rail 42 of approximately 30 to 80 degrees to vertical when viewed in a transverse elevation view. Ultrasonic phased array transducers 150 and 152 may be longitudinally offset to avoid interference between the generated beams 176 and 178. Beam 176 enters rail head 60 on the gauge side 58 and travels across head 60 to the field side 62. Beam 178 enters rail head 60 on the field side 62 and travels across head 60 to the gauge side 58. Beams 176 and 178 detect vertical split head defects. Additionally, ultrasonic phased array transducers 150 and 152 may induce a shear beam, compression beam, or both in the head 60 depending on the rail head shape constraints.

Referring to FIGS. 8 and 14-16, the transducer assembly 138 includes a transducer mount 200 formed from a Noryl® resin blend or other resin. The transducer assembly 138 may include individual ultrasonic transducers or one or more ultrasonic phased array transducers, directed at the rail 42. Preferably, transducer assembly 138 includes a bank of forward-directed ultrasonic transducers 202 and rearward-directed ultrasonic transducers 204 mounted at an angle to produce a beam in the rail of approximately 30 to 60 degrees to vertical in opposite directions. As illustrated, banks 202 and 204 each include four ultrasonic transducers 206, 208, 210, 212, 214, 216, 218, 220, although fewer or more ultrasonic transducers may be used. Each of the ultrasonic transducers 206-220 may be energized independently to emit a forward-directed beam 222 and a rearward-directed beam 224. Beams 222 and 224 penetrate through the web 61 of the rail 42 to the foot 63 to detect defects, such as web and bolt hole cracks, weld defects and centrally located transverse defects. The transducers selected to fire are determined by the rail geometry and known mount alignment, which applies to each bank of ultrasonic transducers.

The transducer assembly 138 may also include conventional transducers 226 and 228, which may be mounted along a longitudinal centerline of transducer mount 200 to produce a refracted sheer wave of about 55 to 85 degrees. The transducers 226 and 228 may be energized to produce ultrasonic beams 230 and 232 at an angle to produce a resultant beam in the rail 42 of approximately 60 to 80 degrees relative to vertical axis Z in opposite directions generally parallel to longitudinal axis X. Beams 230 and 232 detect transverse defects along the transverse axis Y of the rail head 60.

Transducer assembly 138 may include an additional ultrasonic transducer bank 234 mounted at an angle of zero degrees to emit beam 236 substantially vertically through the web 61 to the foot 63. Beam 236 detects defects such as bolt-hole cracks, centrally located defects as well as rail head 60 horizontal and angled defects. The ultrasonic transducers in bank 234 typically operate in pairs of adjacent ultrasonic transducers with one ultrasonic transducer emitting the beam 236 and the other ultrasonic transducer receiving the beam reflection. This pitch/catch combination reduces false returns from internal reflections within the RSU and reflections from the surface of the rail.

Figure 16:
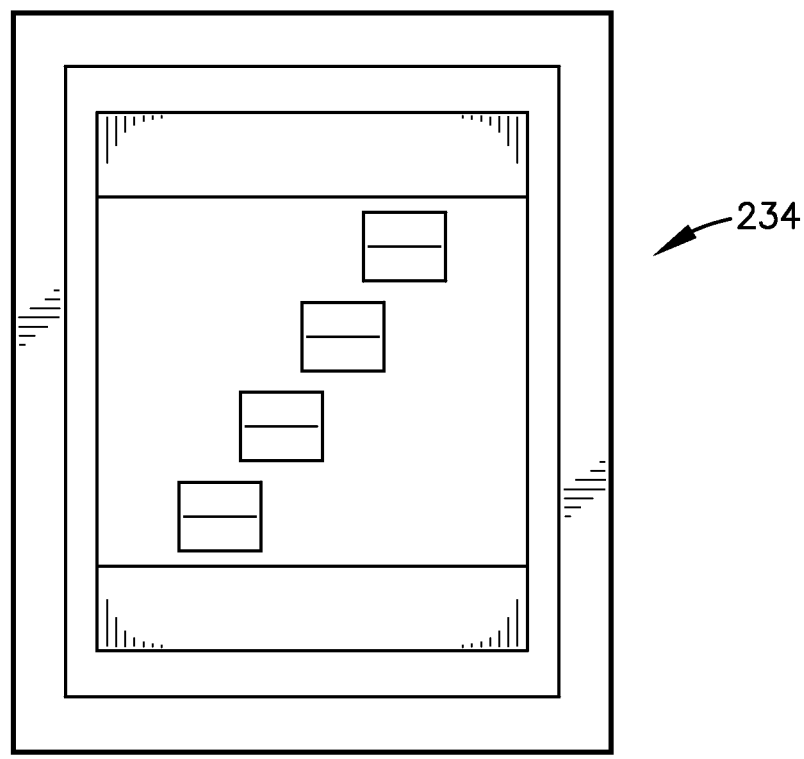
FIG. 16 is a plan view of an ultrasonic transducer assembly.
Figure 21:
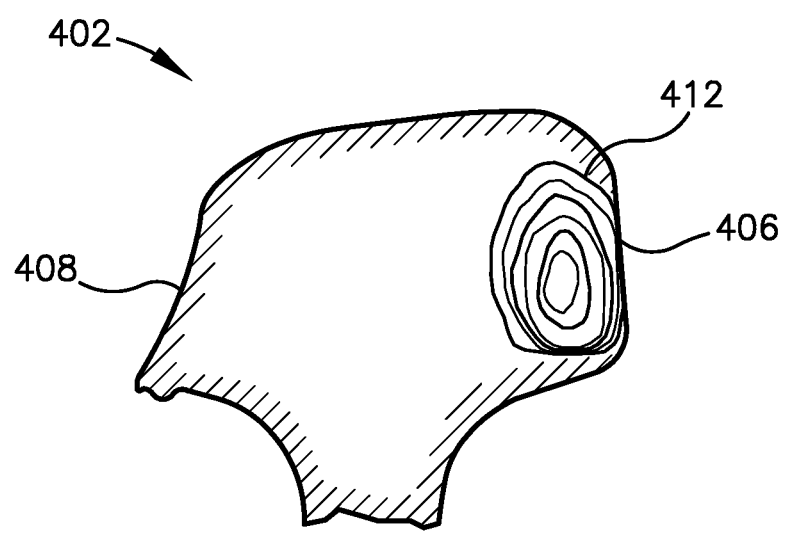
FIG. 21 is an enlarged partial sectional view of a worn rail head illustrating another defect.

The pair of ultrasonic transducers in bank 234 is tightly spaced and may be transversely arranged as illustrated in FIG. 14 or may be longitudinally arranged in a stepped pattern as illustrated in FIG. 16.

To calculate the focal law for each ultrasonic phased array transducer, raw cross section points are determined by the laser transceivers 46 and 48. For simplicity and clarity, the process for one of the transverse pair 46 will be discussed, which will also apply to the other transceiver pair 48.

Referring to FIGS. 2-5, data is received by each of the laser transceivers 54 and 56, which are directed at rail 42. The data points are sent to the system controller 32 along with the encoder data from encoder 30. Each set of data points from the laser transceivers represents a slice of the rail 42 at a given encoder count. The system controller 32 takes the raw data points from each laser transducers 54 and 56 for a given encoder count and processes the points to produce a two-dimensional slice of the rail 42 (see FIG. 4). From the two-dimensional slice, the system controller may determine rail features such as the head 60, web 61, foot 63, gauge surface of the head 65, the field surface of the head 67, the running surface 69, the gauge corner 71, the field corner 73, the gauge side web surface 75 and the field side web surface 77, for example, as well as the feature position and gauge of the rail. Additionally, extraneous material layers such as track structures (i.e. spikes, joint bars, etc.) and other layers such as weeds, and debris are identified and filtered out. Surface normals are calculated and smoothed through interpolation, averaging and plane segment reduction.

Based on the transducer assembly 128 and orientation of each individual ultrasonic transducer array, a range of steering angles is iteratively calculated using ray tracing techniques for each transducer array for each slice 74 of the rail 42, or at a predetermined interval based on time or travel.

For example, for a given ultrasonic transducer array, a trial steering angle is selected for an element within the array. The acoustic interface collisions (time and position) are calculated. Using Snell's law, the refraction or reflection angles are calculated at the interface for a known material, such as steel. The surface normal and acoustic velocities in the material are used to calculate the refraction angle. This calculation is repeated for all interfaces. Next, a target collision is calculated and given a score based on the target proximity and orientation. This process may be repeated for all angles and all elements of the transducer array. The target score determines the selected ray for a given element. Algorithms such as binary ray search may be used to improve processing time or improving the acoustic beam.

For each element of a given array, a total time travel to a common target point is calculated. The travel time for each element is compared to compute the relative delay in firing or energizing each element and receive digitizing delay to steer the resultant beam to the target point. For each profile slice of the rail, or at a fixed time interval, the focal laws are recalculated and compared to the focal laws for the previous profile slice of the rail. If the new focal laws are different than the current applicable focal law, the new focal law may be applied. The difference may be determined on a profile slice-by-profile slice basis, or for calculations falling outside a tolerance or range for the current applicable focal law. In this manner, the beam generated by the ultrasonic transducer array compensates for variations in the running surface 69 of the rail and the resultant effect on the angle of refraction.

For the transducer assembly 138, profile information is used to determine which transducers to fire for any given profile slice. For example, considering transducer bank 202, the beam 222 generated by any of the transducers 206-212, is oriented to penetrate the web 61 of the rail 42 and travel to the foot 63. If no return signal is received, then no defect has been detected. However, in order for the beam 222 to penetrate through the web 61 to the foot 63, the angle of incidence of the beam 222 relative to the surface 69 of the rail head 60 generally should be in a longitudinal plane (Y-Z axes) perpendicular to the plane (X-Z axes) of the running surface 69 and along the centerline 81 of the web 61. If the running surface 69 is not in a horizontal plane or the web 61 is not oriented along the theoretical centerline of a new rail, the beam 222 may "miss" the web 61 and not penetrate to the foot 63.

To compensate for rail wear and variations prevalent in the field with a worn or damaged rail, profile data is used to determine which of the transducers 206-212 will be fired for any given profile slice. Typically, transducers 208 or 210 will likely be fired.

Determination of which of the transducer pairs in the transducer bank 204 and 234 is also based on profile information and calculation of the incident angle which will penetrate the web 61.

Referring to the FIGS. 1-3, and 17-21, as the test vehicle 26 travels along the rails 42 and 44, the laser profiling system 28 scans the rails 42 and 44 and the data is output to the system controller 32. A 2-D profile 74 is generated for each output from the encoder 30 or at a predetermined frequency, and the geometry of each slice 74 is determined. The geometry information is used by the system controller 32 to dynamically calculate the optimal incident angle of a particular ultrasonic beam with respect to the rail head surface and steer the beam based on Huygen's principle and the focal laws. A steering angle for each transducer array may be calculated for each slice 74 or periodically. The calculated steering angle may be dynamically applied for each profile or may be applied when a profile, which is out of range or tolerance for a particular steering angle, persists for two or more calculated profiles.

A focal law table is maintained by the system controller 32 and stored by encoder count. As the test vehicle travels down the rails which corresponds to the longitudinal or X-axis, the ultrasonic transducer system monitors the encoder count and selects the proper focal laws for each cycle. The ultrasonic transducer system delays firing of individual ultrasonic transducer elements within an array a given amount based on the applied focal law table, and delays receiving and sampling by the given amount for each element. The ultrasonic transducer system sums all element responses at appropriate time intervals and constructs an ASCAN per element group. The ASCAN is sent to the system controller 32 along with the encoder data.

The ASCAN data from the ultrasonic transducer system is placed in 3-D by applying time along with the ray tracing calculated in the focal law calculations. The amplitude from the ASCAN may be represented in a number of ways such as color, transparency, and/or disc size, for example. The ASCAN data based on the encoder location data is then represented along with the data from the profiler and the image constructed from the line scan cameras to optionally present a 3-D image of the rail with the location of a defect detected within the rail. Additionally, the 3-D image may be viewed by the operator from any angle, rotating the image as desired, and overlaying camera data to provide additional information to the operator.

When a relevant indication (defect) is detected, the area of the defect may be thoroughly inspected by taking advantage of the phased array's capability to sweep through a range of angles. This can be done in a single arc for a linear arrangement of phased array elements or in multiple dimensions for a matrix or other arrangement of phased array elements. The system controller 32 calculates focal laws to do a targeted sweep of an area at a higher resolution to verify, size and classify the defect. Further, two or more arrays of transducers may be focused on a defect to scan the defect from various angles to provide additional information to better characterize and display the defect.

Figure 4:
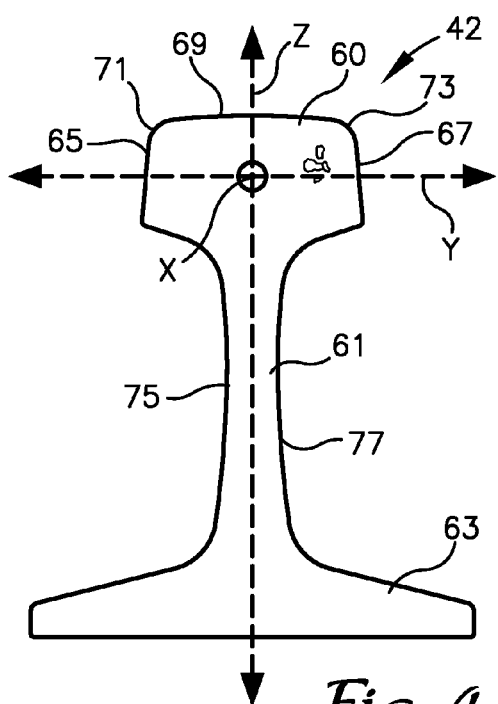
FIG. 4 is a sectional end view of a rail.
Figure 5:
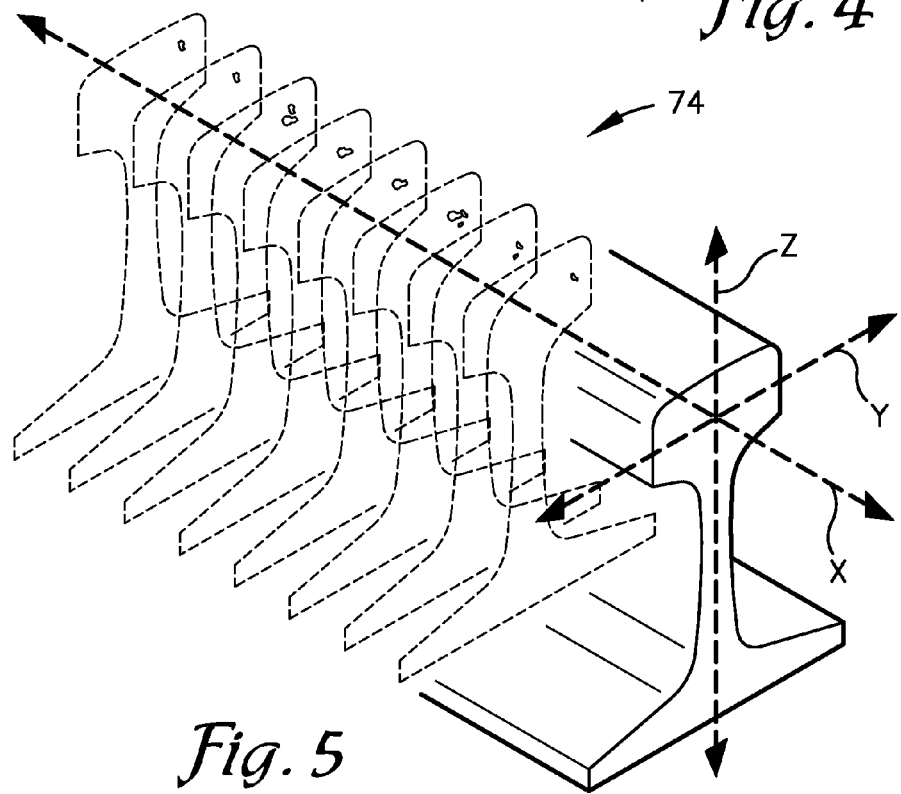
FIG. 5 is an illustration of two-dimensional profile data for a rail.
Figure 6:
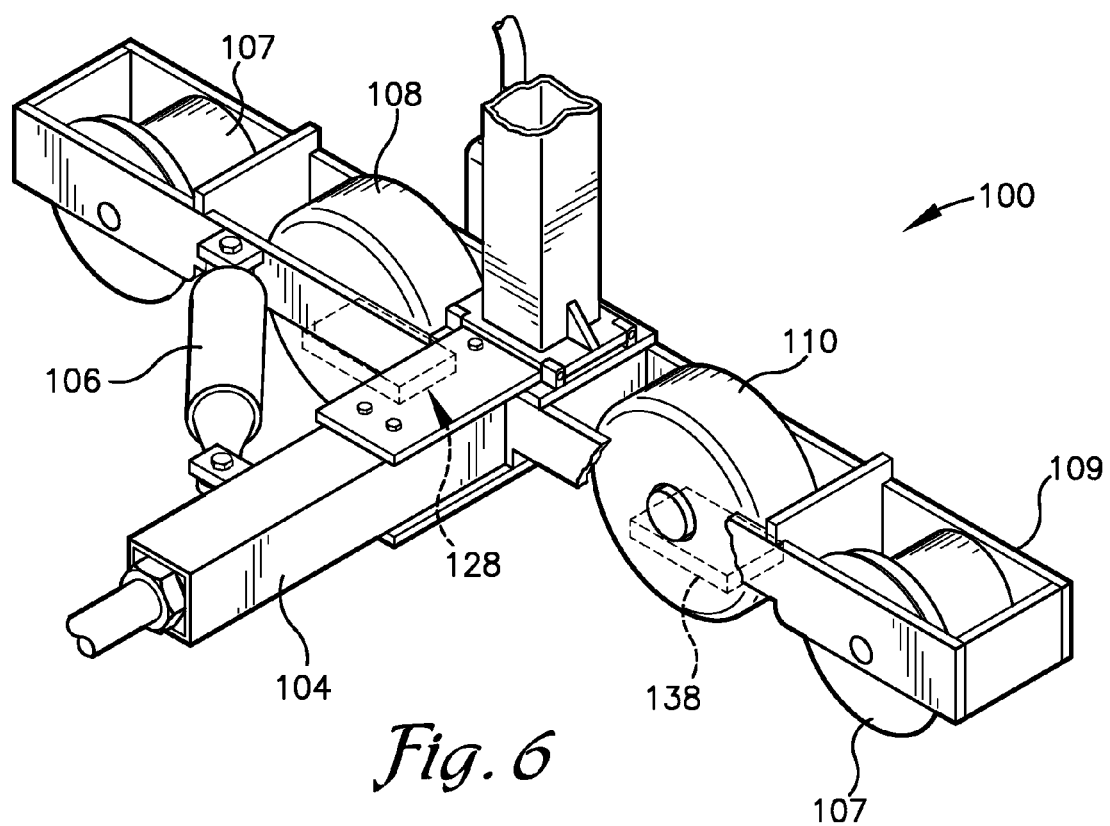
FIG. 6 is a perspective view of a right carriage assembly.
Figure 7:
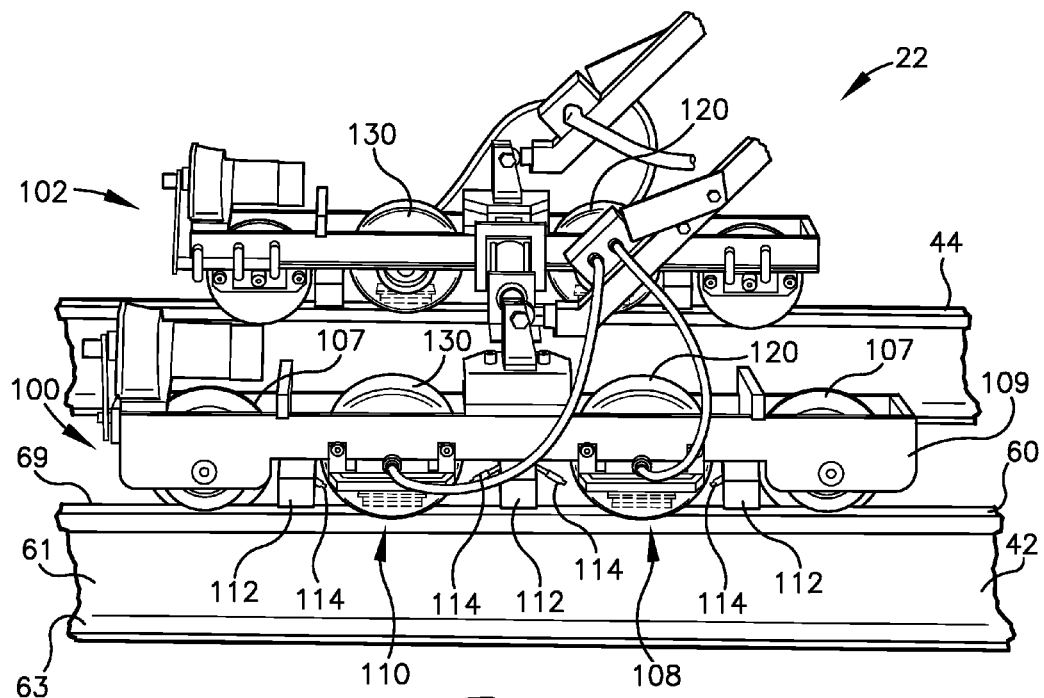
FIG. 7 is a perspective view of the carriage assembly.
Figure 8:
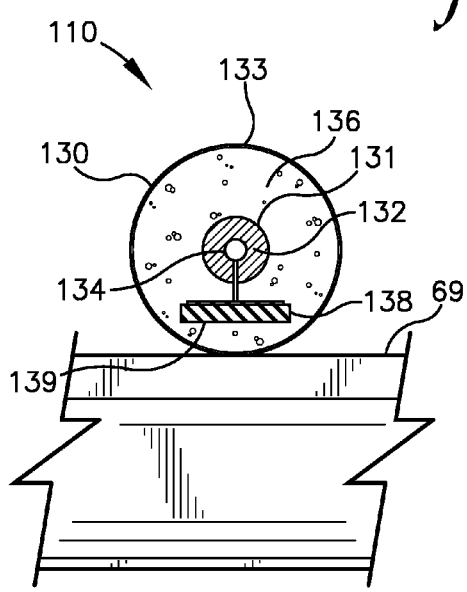
FIG. 8 is a partial sectional view of a first RSU assembly.
Figure 9:
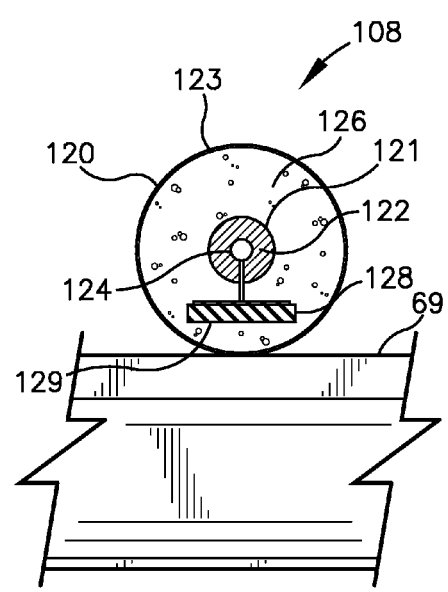
FIG. 9 is a partial sectional view of a second RSU assembly.
Figure 15:
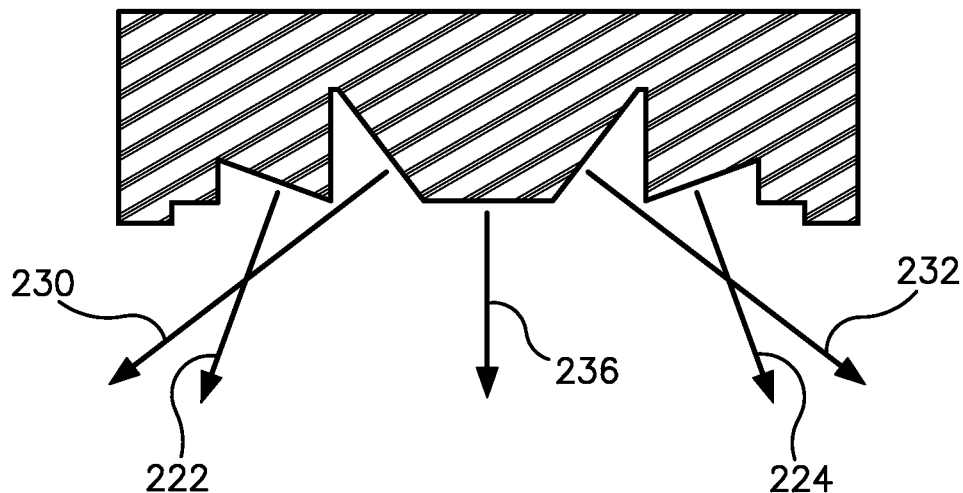
FIG. 15 is a sectional view of the ultrasonic transducer assembly of FIG. 14 along line 15-15.

The rail cross sections illustrated in FIGS. 4 and 5 show a rail profile for an unworn rail 42 with orientation axes X (longitudinal), Y (transverse) and Z (vertical). The rail cross section illustrated in FIG. 18 shows a rail profile for an unworn rail 400. The rail cross sections illustrated in FIGS. 17 and 19-21 show a rail profile for a worn rail 402. Referring to FIG. 18, for the unworn rail 400, the incident angles of beams 160 and 162 are dynamically adjusted by transducer arrays 142 and 146 respectively, to produce resultant beams 161 and 163.

Referring to FIG. 17, for the worn rail 402, the incident angle of beam 160 is dynamically adjusted by transducer array 142 to produce resultant beam 161. The incident angle of beam 162 is dynamically adjusted by transducer array 146 to produce resultant beam 163.

Referring to FIG. 19, for the worn rail 402, the incident angle of beam 168 is dynamically adjusted by transducer array 142 to produce resultant beam 169. The incident angle of beam 170 is dynamically adjusted by transducer array 146 to produce resultant beam 171. Because of the worn rail head 406 on the gauge side 408 of the rail head 406 the angle of incident (the primary steering angle) is adjusted by steering the beam to achieve the desired angle of refraction in the rail head 406.

If a defect 410 or 412 for example, is detected, information such as the characteristics of the defect, location, image information at the location of defect, and geometry of the defect may be stored. Additionally, the system controller 32 may direct one or more phased array transducers in the second or additional trailing RSUs to scan or sweep the area of a defect detected by the first RSU 108 to obtain additional information regarding the defect. The defect location in the head, or anywhere a defect is located, may be displayed graphically along with the profile and line scan camera data to provide the operator with a 3-D image that may be manipulated, rotated and viewed from any orientation or angle. The defect may be viewed from any vantage point outside the rail or may be viewed from within the rail. The size of the defect 410 or 412, for example, may be represented by concentric rings around the defect or by colors to provide additional information to the operator.

It is to be understood that while certain now preferred forms of this invention have been illustrated and described, it is not limited thereto except insofar as such limitations are included in the following claims.

Having thus described the invention, what is claimed as new and desired to be secured by Letters Patent is as follows:

1. A method for inspecting a railway rail comprising:
   constructing a profile of the rail;
   determining a steering angle for one or more phased array transducer elements from said rail profile;
   energizing one or more ultrasonic phased array transducer elements; and
   emitting an ultrasonic beam from said ultrasonic phased array transducer at said steering angle into the rail;
   wherein each of the above steps is performed on or directed by a programmed computer.

2. The method of claim 1 further comprising transmitting a laser signal toward the rail and receiving a reflected laser signal.

3. The method of claim 2 wherein said constructing a profile step includes constructing a profile from said reflected laser signal.

4. The method of claim 2 wherein said transmitting step includes first and second laser transceivers, wherein said first laser transceiver is directed toward a field side of the rail and said second laser transceiver is directed toward a gauge side of the rail.

5. The method of claim 1 wherein said constructing step includes determining surface normals for said profile.

6. The method of claim 5 wherein said constructing step includes determining focal laws for a desired angle of refraction based on said surface normals for said profile.

7. The method of claim 1 wherein said constructing step includes constructing a plurality of profiles of the rail.

8. The method of claim 1 wherein said determining step includes determining two or more steering angles.

9. The method of claim 1 wherein said determining step includes calculating delay laws to enable said steering angle to a target.

10. The method of claim 1 further comprising receiving a reflected ultrasonic beam indicative of a defect within the rail.

11. The method of claim 10 further comprising assembling a plurality of profiles and one or more defects within the rail to present a three dimensional representation of said one or more defects within the rail.

12. The method of claim 1 further comprising capturing an image of the rail.

13. The method of claim 12 wherein said profile is combined with said image to present a three dimensional image of the rail.

14. A method for inspecting a railway rail comprising:
   constructing a profile of the rail using one or more laser transceivers;
   determining surface normals for said rail profile;
   determining focal laws for a desired angle of refraction from said surface normals;
   determining a steering angle for one or more phased array transducer elements from said rail profile;
   energizing one or more ultrasonic phased array transducer elements; and
   emitting an ultrasonic beam from said ultrasonic phased array transducer at said steering angle into the rail;
   wherein each of the above steps is performed on or directed by a programmed computer.

15. The method of claim 14 wherein said constructing step includes first and second laser transceivers, wherein said first laser transceiver is directed toward a field side of the rail and said second laser transceiver is directed toward a gauge side of the rail.

16. The method of claim 14 wherein said determining a steering angle step includes determining two or more steering angles.

17. The method of claim 14 wherein said determining a steering angle step includes calculating delay laws to enable said steering angle to a target.

18. The method of claim 14 further comprising receiving a reflected ultrasonic signal indicative of a defect within the rail.

19. The method of claim 18 further comprising assembling a one or more reflected ultrasonic signals indicative of one or more defects within the rail to present a three dimensional representation of said one or more defects within the rail.

20. The method of claim 14 further comprising capturing an image of the rail and combining said image with said profile and three dimensional representation of said one or more defects to present a three dimensional image of the rail and said one or more defects within the rail.

* * * * *